United States Patent [19]

Parins

[11] Patent Number: 5,217,458
[45] Date of Patent: Jun. 8, 1993

[54] BIPOLAR BIOPSY DEVICE UTILIZING A ROTATABLE, SINGLE-HINGED MOVING ELEMENT

[75] Inventor: David J. Parins, Columbia Heights, Minn.

[73] Assignee: Everest Medical Corporation, Minneapolis, Minn.

[21] Appl. No.: 866,191

[22] Filed: Apr. 9, 1992

[51] Int. Cl.$^5$ ............................................. A61B 17/39
[52] U.S. Cl. ........................................ 606/48; 606/1;
606/39; 606/45; 606/50; 128/362; 128/751;
128/783; 128/790
[58] Field of Search ............... 128/783, 362, 790, 751,
128/401, 402; 606/1, 27, 29, 32, 39, 40, 45–52,
170, 180

[56] References Cited

U.S. PATENT DOCUMENTS

| | | |
|---|---|---|
| 659,409 | 10/1900 | Mosher . |
| 1,952,617 | 3/1934 | Wappler . |
| 2,011,169 | 8/1935 | Wappler . |
| 2,031,682 | 2/1936 | Wappler et al. . |
| 4,655,216 | 4/1987 | Tischer . |
| 4,953,559 | 9/1990 | Salerno . |
| 4,976,711 | 12/1990 | Parins et al. . |
| 5,085,659 | 2/1992 | Rydell ................................. 606/48 |

Primary Examiner—Stephen C. Pellegrino
Assistant Examiner—Glenn K. Dawson
Attorney, Agent, or Firm—Haugen and Nikolai

[57] ABSTRACT

A bipolar biopsy device for removing tissue samples for biopsy purposes or other purposes. The bipolar biopsy device has an elongated flexible end and a lumen extending therebetween. A cutting head is mounted on the distal end and has a hollow fixed member containing an electrode having an electrical surface thereon and a hollow cup-shaped moveable relative to the fixed member. The electrode surfaces are electrically connected to an outside voltage source. A handle is affixed to the proximal end and a core wire is affixed to the handle which extends through the lumen and is affixed to the movable hollow cup-shaped member. The core wire manipulated by way of the handle facilitates the movement of the movable cup-shaped member. Tissue samples are obtained by positioning the electrode surfaces close to each other about the tissue sample. An arc is created to break tissue down by applying a voltage to the 2 electrode surfaces. The cut tissue remains within the cup-shaped members as the device is withdrawn from the body for later biopsy purposes.

27 Claims, 2 Drawing Sheets

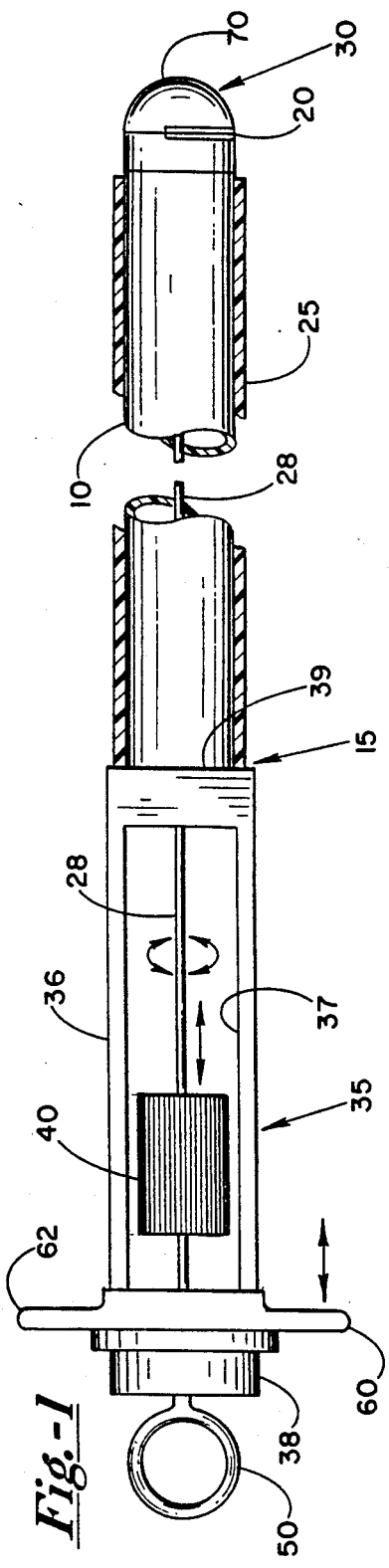
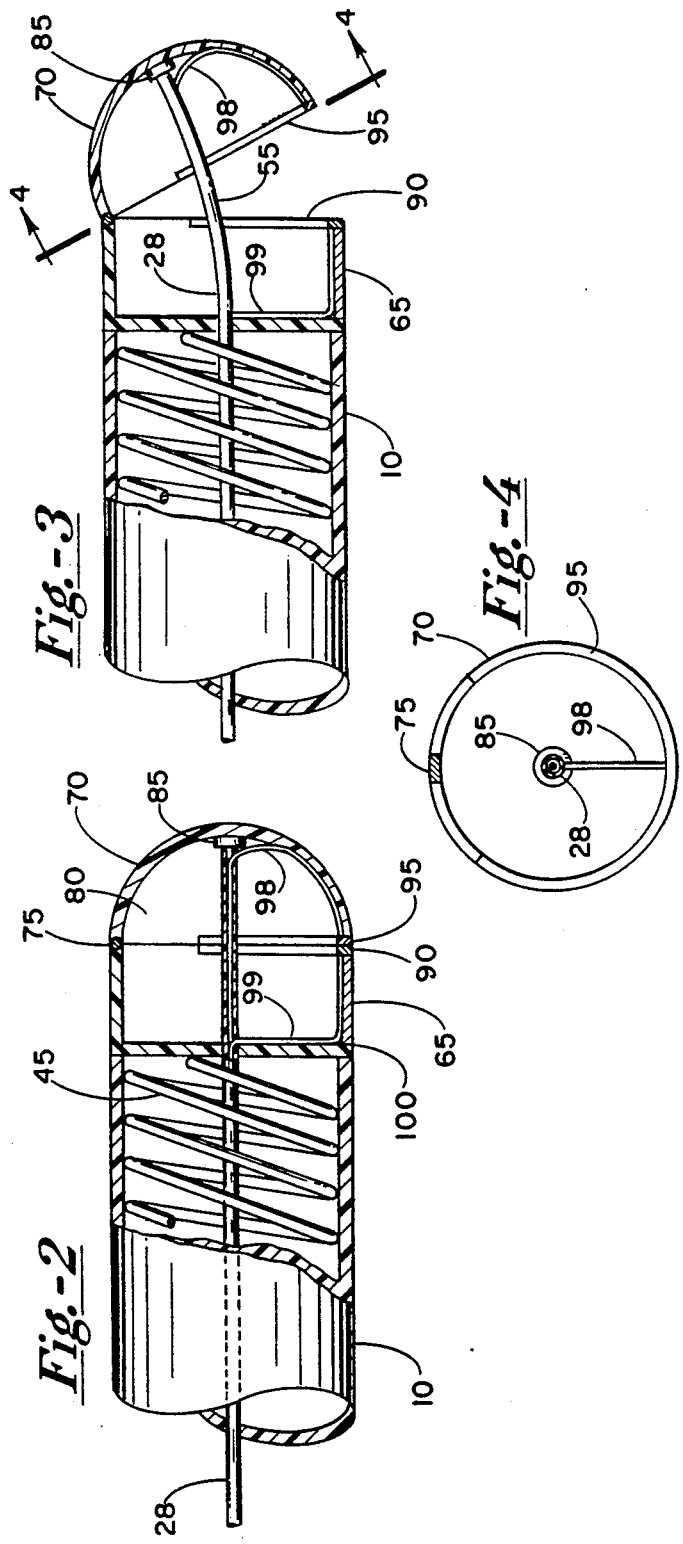

BIPOLAR BIOPSY DEVICE UTILIZING A ROTATABLE, SINGLE-HINGED MOVING ELEMENT

FIELD OF THE INVENTION

The present invention relates to bipolar biopsy devices and, in particular, to a bipolar biopsy device utilizing a rotatable, single hinged or unhinged moving element for its cutting head.

BACKGROUND OF THE INVENTION

Obtaining tissue samples for diagnostic purposes is a commonly performed surgical procedure known as a biopsy. Such a procedure requires two steps: cutting a tissue sample and then retrieving the cut sample. Electrosurgical devices are a well known surgical instrument. Such devices cut the tissue by applying a voltage across two electrodes, creating an arc discharge which creates such a high heat energy that the cells comprising the tissue break down. Electrosurgical cutting has been utilized on catheters for a less invasive procedure such as shown in U.S. Pat. No. 4,976,711 to Parins et al.

The prior art has shown various ways to retrieve the cut tissue. U.S. Pat. No. 4,655,216 to Tischer utilizes an open ended basket. U.S. Pat. No. 4,953,559 to Salerno utilizes a cup shaped forceps on the end of a linkage arm.

What is needed is a biopsy device which is minimally invasive by utilizing electric surgical cutting and coagulating and a means to retrieve the cut tissue sample without the complicated linkage arms.

Therefore the primary object of the present invention is to provide a bipolar biopsy device providing for electrosurgical cutting and coagulation by way of a catheter containing a cutting electrode which is moveable by manipulation of a core wire.

Another object of the invention is to utilize a rotatable, single-hinged moving element having mating electrodes for the cutting head.

Yet another object of the invention is to provide a biopsy device with a RF cutting/coagulating head on the distal end of a catheter, the head having a member reciprocably moveable relative to a member fixed to the catheter by utilizing a core wire running the length of the catheter.

Another object of the invention is to provide a bipolar electrode biopsy device having varying means for rotationally journaling the cutting head.

SUMMARY OF THE INVENTION

The present invention is a device for performing a cutting operation electrosurgically and especially designed to capture a severed tissue sample for subsequent analysis. The device comprises an elongated tube having a specially designed cutting head on the distal end thereof. In accordance with a first embodiment the cutting head is rotatably mounted on the distal end of the tube. By rotating a central core wire, the cutting head can be made to spin or rotate 360 degrees.

The head itself comprises a fixed member and a movable member pivotally secured to the fixed member. A first electrode surface is provided on the fixed member and a corresponding second electrode surface on the movable member. When the two electrode surfaces are brought together about a piece of tissue, and an appropriate RF voltage is applied to the instrument, electrosurgical cutting or coagulation can take place. The movable member is opened and closed by advancing and retracting a core wire. The cut tissue sample is captured in a cup-like cavity formed within the fixed and movable member.

In an alternative embodiment the movable member is affixed to the end of the core wire and movable longitudinally therewith instead of being pivotally coupled to the fixed member. The movable member can be advanced and retracted longitudinally to an electrode surface on the fixed member of the instrument. By appropriate manipulation of the core wire at its proximal end. The electrode surfaces extend along the entire circumference of each cutting head member, thereby eliminating the need for rotational movement.

DESCRIPTION OF THE DRAWINGS

The foregoing features and advantages of the invention will become apparent to those skilled in the art from the following detailed description of the present invention, in which like numerals in the several views refer to corresponding parts.

FIG. 1 is a partial side sectional view showing the proximal and distal ends of the electrosurgical biopsy device of the present invention.

FIG. 2 is an enlarged view of the distal portion of the device of FIG. 1 showing the cutting head in its closed position.

FIG. 3 is an enlarged view of the distal portion of the invention of FIG. 1 showing the cutting head in an open position.

FIG. 4 is a view taken along line 4—4 of FIG. 3.

DESCRIPTION OF THE PREFERRED EMBODIMENT

Figure 5:
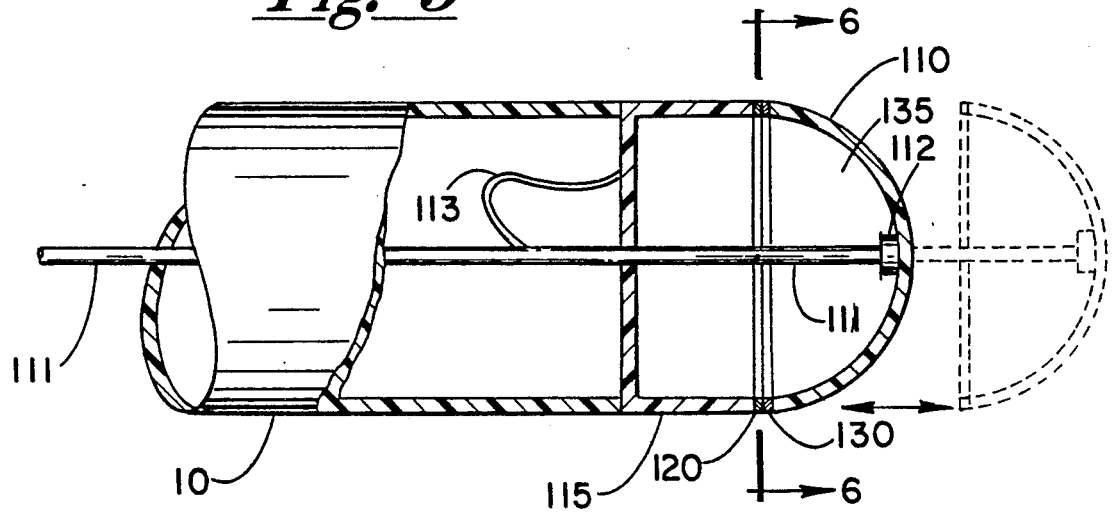
FIG. 5 is an enlarged view of the distal portion of an alternative embodiment in a closed position with broken lines showing an open position.

FIG. 1 depicts the general configuration of the bipolar biopsy device which is indicated generally by numeral 5 and utilizes a rotatable, single-hinged, pivotable element. The device has an elongated, flexible tubular member 10 having a proximal end 15, a distal end 20, and a cutting head 30. The tubular member 10 is surrounded by a sheath 25. A core wire 28 extends through the lumen of the tubular member 10. Affixed to the distal end 20 is a rotatable, single-hinged moving element which comprises the head 30 and which will be more fully described later in this specification.

Affixed to the proximal end of the tubular member 10 is a handle indicated generally by numeral 35. The handle preferably comprised a molded plastic cylindrical body 36 having a longitudinal slot 37 formed therethrough and disposed within the slot is a knurled knob 40 for providing rotational movement to the cutting head 30. More particularly, knob 40 is affixed to a core wire 28 which passes loosely through aligned apertures formed in the proximal end 38 and to distal end 39 of the handle 35. A core wire 28 provides rotational movement to the cutting head 30. As will be appreciated by those skilled in the art, a spring 45 is conventionally attached to the cutting head so as to act as a bearing means when the core wire rotates the cutting head 30. Rotation of the core wire causes the cutting head 30 to rotate at the distal end of the tubular member 10. In addition to rotational movement, reciprocal movement is provided to a portion of the cutting head by way of core wire 28. A thumb-engageable ring member 50 of the handle 35 is manipulated to impart reciprocal movement to the core wire and the knurled knob is manipulated to impart rotational movement to the core wire 28. The handle 35 contains finger flanges 60 and 62 for ease in gripping the handle and manipulating ring. Also connected to the handle and not shown is means for connecting the device to a voltage source.

The tubular member 10 and sheath 25 are made from a medical grade plastic such as nylon, polyethylene or TEFLON ® polypropylene. The tubular member 10 can be withdrawn into the sheath 25 during introduction of the bipolar biopsy device 5 into a body lumen or cavity.

The cutting head consists of a fixed member 65 abutting the distal end of the tubular member 10 and movable member 70 pivotally attached to the fixed member. In the first embodiment, shown in FIGS. 2 and 3, the movable member 70 has a hollow hemispherical or cup shape and is pivotally hinged to the hollow fixed member at 75. When the cutting head 30 is in the closed position, a closed cavity 80 is formed therein the fixed member 65 is capable of only rotational movement above the distal end of the tubular member 10. The core wire 28 is connected to the movable cup member as shown at 85. A first electrode surface 90 is located on the fixed member 65 and a second electrode surface is located on the movable member 70. The electrodes are ideally made of tungsten or stainless steel but other materials may also be used. The electrode surface does not extend around the entire circumference of the moveable or fixed member. As shown in FIG. 4, the edges of the surface are separated by about a 90° angle. This optimal angle ensures the proper arc is created without creating a short circuit at the hinged area.

Core wire 28 is connected to an outside voltage source not shown and contains two wires 98 and 99 insulated from each other for applying the voltage across the first and second electrical surfaces. A first lead 100 runs from the core wire 28 to the first electrode surface 90 on the fixed member 65 and a second lead 98 (FIG. 4) runs from the core wire 28 to the second electrode surface 95. The two insulated wires do not need to be contained within the core wire 28. Other arrangements, such as having the wires separately extend through the tubular member, are acceptable.

Figure 6:
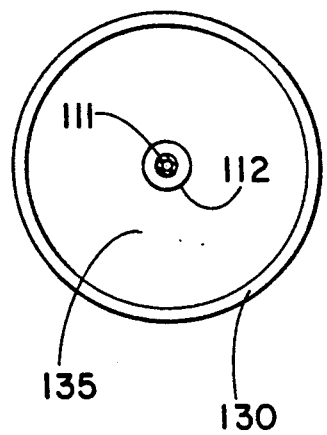
FIG. 6 is a view taken along line 6—6 of FIG. 5.

In the alternative embodiment shown in FIG. 5 the movable member 110 is not pivotally hinged to the fixed portion 115 and does not contain a bearing means for supporting the cutting head assembly in rotation. Instead, the movable member 110 is connected to the device by means of the core wire 111 attached at 112. Like the cutting head of the first embodiment, the fixed member 115 is generally hollow. However, in this embodiment the entire fixed member 120 operates as the first electrode and can be conveniently fabricated from a suitable metal. As before, the movable member 110 has a hollow cup shape and operates as the second electrode 130. The electrodes on both members extend about the entire circumference as shown in FIG. 6.

As with the first embodiment, two insulated wires extending through the lumen of the member 10 are necessary to connect the electrodes to the voltage source (not shown). Furthermore, the two wires are not restricted to the core wire interior. Other suitable arrangements, such as having the wires separately extend through the tubular member, are acceptable.

In operation, and first considering the embodiment of FIGS. 1-3, the elongated tube 10 and cutting head 30 within the sheath 25 are routed through the patient to the area to be electrosurgically cut. Upon reaching the site, the cutting head 30 is advanced distally relative to the sheath 25 until the head is exposed. The movable member 70 is opened relative to the fixed member 65 by manipulating the core wire 28 using the thumbring 50 on the handle 35 and a tissue sample for later biopsy procedures is positioned between the two electrode surfaces 90 and 95. As the electrodes are closed relative to one another and a voltage is applied to the electrode surfaces, an arc is created therebetween for cutting the tissue. The cutting head 30 may then be completely closed, thereby retaining the cut tissue within the cavity portion 80 as it is drawn into the sheath 25. The cutting head 30 and elongated tube 10 may be removed from the body while retaining the tissue within the cutting head 30 for later biopsy purposes. It is also possible to obtain multiple samples by repeating the above procedure but without withdrawing the instrument between cuttings. The moveable member 70 is opened and closed by advancing and retracting the core wire 28 by manipulation of ring member 50 on the handle. The rotational knob 40 and bearing means (spring 45) allow the operator to rotate the cutting head 35 in its cutting location for obtaining tissue samples nearby without moving the entire tubular member 10 and sheath 25 within the patient's body.

The alternative embodiment shown in FIG. 5 operates as follows. When the core wire 28 is manipulated with the thumbring, the entire moveable 110 member can be reciprocated, thus enabling the cutting head to first be opened wider and then closed after a tissue sample is selected for excision. Furthermore as shown in FIG. 6, because the segments 110 and 115 are fabricated totally from metal, electrode surfaces 120 and 130 extend completely around the circumference of the fixed and moveable members since.

The invention is versatile and can be used for non-biopsy surgical procedures such as removing plaque deposits in blood vessels, removing polyps from the intestinal wall and other comparable procedures.

The invention has been described here in considerable detail in order to comply with the patent statutes and to provide those skilled in the art with the information needed to apply the novel principles and to construct and use such specialized components as are required. However, it is to be understood that the invention can be carried out by specifically different equipment and devices, and that the various modifications, both as to the equipment details in operating procedures, can be accomplished without departing from the scope of the invention itself.

What is claimed is:

1. A bipolar device comprising:
   a. an elongated flexible tubular member having proximal end, a distal end, and a wall defining a lumen extending from said proximal end to said distal end;
   b. a handle means affixed to said proximal end of said tubular member for facilitating gripping of said device;
   c. a core wire extending through said lumen, said core wire slidably and rotatably mounted within said handle;

d. a cutting head rotatably mounted on the distal end of said tubular member, said cutting head comprising:
  i. a first hollow cup member having a electrode surface thereon and rotatably mounted on said distal end of said tubular member;
  ii. a second hollow cup member having a second electrode surface thereon and movable relative to said first hollow cup member, said second hollow cup member coupled to said core wire;
e. bearing means for rotationally supporting said cutting head relative to said distal end of said tubular member; and
f. conductor means extending from said proximal end of said tubular member to said first and second electrode surfaces for applying a voltage across said first and second electrode surface.

2. A bipolar biopsy device of claim 1 wherein said conductor means includes a first and second elongated wires insulated from each other said first wire of said conductor means being electrically joined to said first electrode surface and said second wire being electrically joined to said second electrode surface.

3. The bipolar biopsy device of claim 1 wherein said electrode surfaces are tungsten.

4. The bipolar biopsy device as in claim 1 wherein said conductor means comprise said core wire.

5. The bipolar biopsy device as in claim 1 wherein said tubular member is made from a medical grade plastic.

6. The bipolar biopsy device as in claim 1 further including a tubular sheath surrounding said tubular member.

7. The bipolar biopsy device as in claim 6 wherein said tubular sheath is made from a medical grade plastic.

8. The bipolar biopsy device of claim 1 wherein said core wire is coaxially aligned within said tubular member.

9. The bipolar biopsy device of claim 1 wherein said bearing member is a spring.

10. The bipolar biopsy device of claim 1 wherein said second hollow cup member is pivotally attached to said first hollow cup member.

11. The bipolar biopsy device of claim 1 wherein said first hollow cup member is fixedly attached to said bearing means, said bearing means frictionally engaging said wall of said tubular member.

12. The bipolar biopsy device of claim 1 wherein said second hollow cup member is reciprocally moveable relative to said first hollow cup member.

13. A bipolar biopsy device comprising:
a. an elongated, flexible tubular member having a proximal end, a distal end, and a wall defining a lumen extending from said proximal end to said distal end;
b. a cutting head mounted on said distal end of said tubular member, said cutting head comprising:
  i. a first hollow cup member having a first electrode surface;
  ii. a second hollow cup member having a second electrode surface;
c. a handle means affixed to said proximal end of said tubular member for facilitating gripping of said device;
d. a core wire extending through said lumen, said core wire connected to interior of said second hollow cup member and slidable relative to said handle means; and
e. conductor means extending from said proximal end of said tubular member to said first and second electrodes for applying a voltage across said first and second electrodes.

14. The bipolar biopsy device of claim 13 wherein said electrode surface are tungsten.

15. The bipolar biopsy device of claim 13 wherein said cutting head has a diameter at most the diameter of said tubular member.

16. The bipolar biopsy device of claim 13 wherein said tubular member is made from a medical grade plastic.

17. The bipolar biopsy device of claim 13 wherein said core wire comprises said conductor means and includes a first and second elongated wires insulated from each other with the first wire electrically joined to said first electrode surface and said second wire electrically joined to said second electrode surface.

18. The bipolar biopsy device of claim 13 further including a tubular sheath surrounding said tubular member.

19. The bipolar biopsy device of claim 18 wherein said tubular sheath is made from a medical grade plastic.

20. The bipolar biopsy device of claim 1 wherein said core wire is coaxially aligned within said tubular member.

21. A bipolar biopsy device comprising:
a. an elongated, flexible tubular member having a proximal end, a distal end, and a wall defining a lumen extending from said proximal end to said distal end;
b. a cutting head rotatably mounted on said distal end of said tubular member, said cutting head comprising:
  i. a first hollow cup member having a first electrode surface;
  ii. a second hollow cup member moveable relative to said first hollow cup member and having a second electrode surface;
c. a handle means affixed to said proximal end of said tubular member for facilitating gripping of said device;
d. a core wire extending through said lumen, said core wire connected to interior of said second hollow cup member for providing reciprocal movement thereto and slidably mounted to said handle; and
e. conductor means extending from said proximal end of said tubular member to said first and second electrodes for applying a voltage across said first and second electrodes.

22. A bipolar biopsy device of claim 21 wherein said core wire includes said conductor means, said conductor means comprising a first and second elongated wires insulated from each other, said first wire of said conductor means being electrically joined to said first electrode surface and said second wire of said conductor means electrically joined to said second electrode surface.

23. The bipolar biopsy device of claim 21 wherein said electrode surfaces are tungsten.

24. The bipolar biopsy device of claim 21 wherein said tubular member is made from a medical grade plastic.

25. The bipolar biopsy device of claim 21 further including a tubular sheath surrounding said tubular member.

26. The bipolar biopsy device of claim 25 wherein said tubular sheath is made from a medical grade plastic.

27. The bipolar biopsy device of claim 21 wherein said core wire is coaxially aligned within said tubular member.

* * * * *